US012571722B2

(12) United States Patent
Garlan et al.

(10) Patent No.: US 12,571,722 B2
(45) Date of Patent: Mar. 10, 2026

(54) GEOLOGICAL SAMPLE SCANNING SYSTEM

(71) Applicant: PlotLogic Pty Ltd, Queensland (AU)

(72) Inventors: Matthew Garlan, Queensland (AU); Andrew Job, Queensland (AU)

(73) Assignee: PlotLogic Pty Ltd, Queensland (AU)

( * ) Notice: Subject to any disclaimer, the term of this patent is extended or adjusted under 35 U.S.C. 154(b) by 59 days.

(21) Appl. No.: 18/290,005

(22) PCT Filed: Jul. 11, 2022

(86) PCT No.: PCT/AU2022/050724
§ 371 (c)(1),
(2) Date: Nov. 8, 2023

(87) PCT Pub. No.: WO2023/283680
PCT Pub. Date: Jan. 19, 2023

(65) Prior Publication Data
US 2024/0241037 A1      Jul. 18, 2024

(30) Foreign Application Priority Data

Jul. 12, 2021    (AU) ................................. 2021104062

(51) Int. Cl.
*G01N 21/01*      (2006.01)
*F16M 11/04*      (2006.01)
(Continued)

(52) U.S. Cl.
CPC ........... *G01N 21/01* (2013.01); *F16M 11/048* (2013.01); *F16M 11/18* (2013.01); *F16M 11/24* (2013.01);
(Continued)

(58) Field of Classification Search
CPC .................. G01N 21/01; G01N 33/24; G01N 2021/0106; G01N 21/27; G01N 21/84;
(Continued)

(56) References Cited

U.S. PATENT DOCUMENTS 11,112,682 B1 *   9/2021   Quinta Gaspar ...... F16M 11/08
2008/0308727 A1   12/2008  Boguslavsky et al.
(Continued)

FOREIGN PATENT DOCUMENTS

CN          206594166        10/2017
CN          109187361         1/2019
(Continued)

OTHER PUBLICATIONS

AU AU2021104062 Exam Rept., Oct. 28, 2021, PlotLogic Pty Ltd.
(Continued)

*Primary Examiner* — Hung V Nguyen
(74) *Attorney, Agent, or Firm* — Wells St. John P.S.

(57)          ABSTRACT

The present invention relates to a geological sample scanning system to be disassembled for transport and then re-assembled onsite at a mine site or field. The system includes a stand. An imaging sensor is provided for being supported by the stand. The system also includes a transporter for transporting a geological sample, in the form of ore from the mine site or field, along a single axis to be sensed by the sensor.

20 Claims, 1 Drawing Sheet

(B)

(C)

(A)

(D)

(51) Int. Cl.
  *F16M 11/18*  (2006.01)
  *F16M 11/24*  (2006.01)
  *G01N 33/24*  (2006.01)
  *H04N 23/12*  (2023.01)
  *H04N 23/56*  (2023.01)

(52) U.S. Cl.
  CPC ............. *G01N 33/24* (2013.01); *H04N 23/12* (2023.01); *H04N 23/56* (2023.01); *G01N 2021/0106* (2013.01)

(58) Field of Classification Search
  CPC ...... F16M 11/048; F16M 11/18; F16M 11/24; F16M 11/425; H04N 23/12; H04N 23/56; H04N 23/11; G03B 17/561; G03B 37/02
  See application file for complete search history.

(56)                References Cited

U.S. PATENT DOCUMENTS

| | | | | |
|---|---|---|---|---|
| 2010/0200710 | A1* | 8/2010 | Shenouda | .............. F16M 13/00 248/157 |
| 2014/0327760 | A1 | 11/2014 | Kurz et al. | |
| 2021/0150695 | A1 | 5/2021 | Yogo | |
| 2021/0223153 | A1* | 7/2021 | Zhao | .................. G01B 11/2545 |
| 2023/0003918 | A1 | 1/2023 | Job et al. | |

FOREIGN PATENT DOCUMENTS

| | | | | |
|---|---|---|---|---|
| CN | 109269948 | | 1/2019 | |
| CN | 208567951 | | 3/2019 | |
| EP | 3640584 | | 4/2020 | |
| WO | WO 2020/032905 | | 2/2020 | |
| WO | WO-2020032905 | A2 * | 2/2020 | .......... B07C 5/3425 |
| WO | WO 2021/108838 | | 6/2021 | |
| WO | PCT/AU2022/050724 | | 3/2023 | |

OTHER PUBLICATIONS

PCT/AU2022/050724 Search Rept., Sep. 30, 2022, PlotLogic Pty Ltd.

PCT/AU2022/050724 Writ. Opin., Sep. 30, 2022, PlotLogic Pty Ltd.

\* cited by examiner

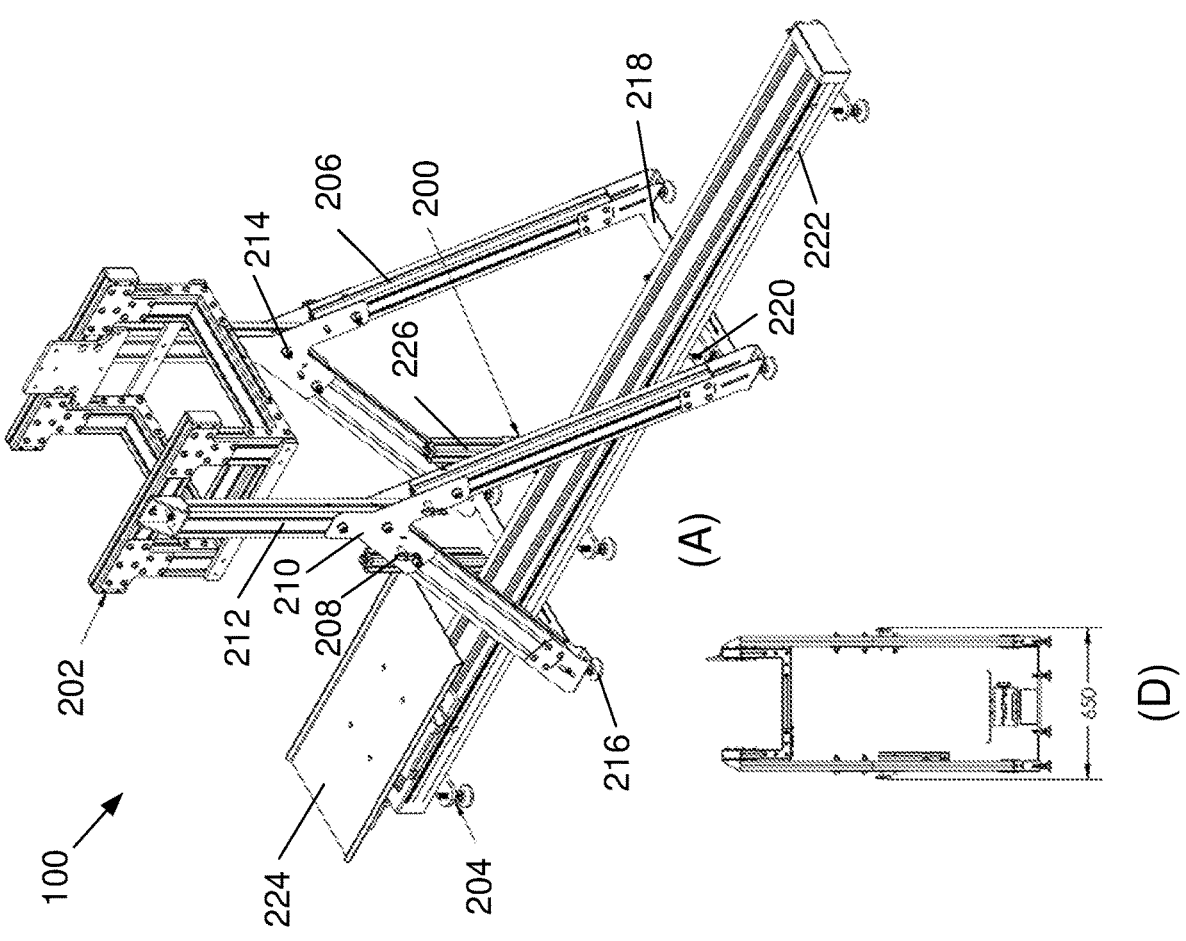
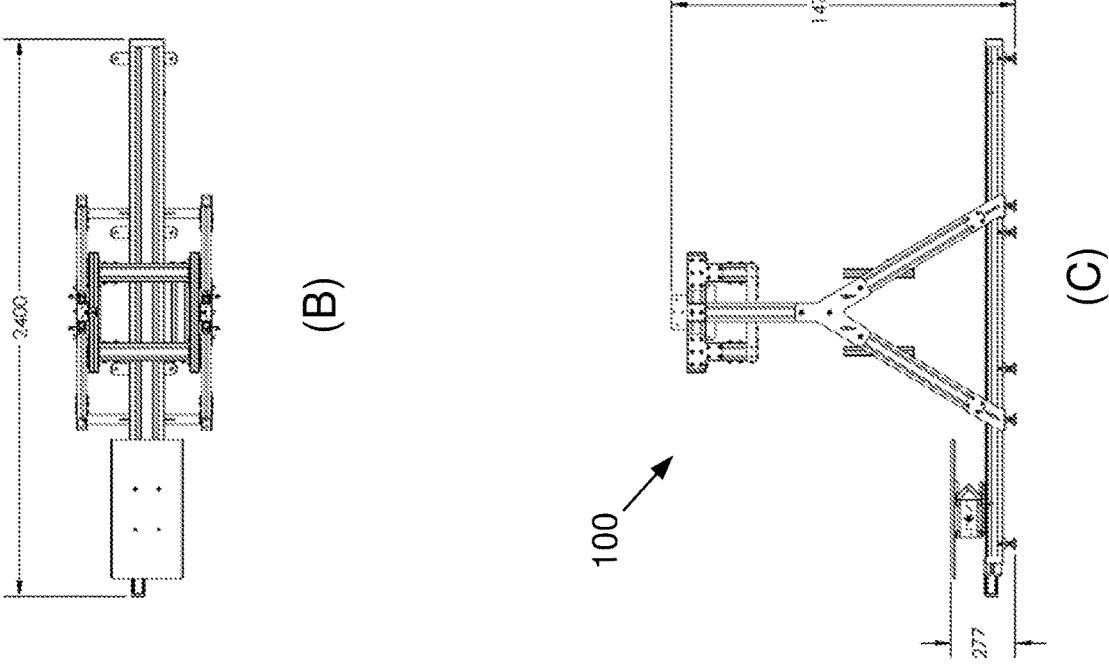

GEOLOGICAL SAMPLE SCANNING SYSTEM

RELATED PATENT DATA

This application is a 35 U.S.C. § 371 of and claims priority to PCT International Application Number PCT/AU2022/050724, filed 11 Jul. 2022, which was published in English, and which claims priority to AU patent application Ser. No. 2021104062, filed 12 Jul. 2021, the teachings of which are incorporated herein by reference.

TECHNICAL FIELD

The present invention relates to a geological sample scanning system.

BACKGROUND

The reference to any prior art in this specification is not, and should not be taken as an acknowledgement or any form of suggestion that the prior art forms part of the common general knowledge.

PCT/AU2020/051275 discloses a mobile mining spectral scanner for detecting changes in the ore grade of a rock face in near real time. In practice, such spectral scanners are calibrated before use. Invariably, it is also desirable to validate the performance of a material characterization algorithm.

Scanning systems are known for calibrating the scanner sensor and validating algorithms in the field. However, such systems are unwieldy to transport to site, and not suited to frequent moving from site to site.

The preferred embodiment provides an improved scanning system.

SUMMARY OF THE INVENTION

According to one aspect of the present invention, there is provided a geological sample scanning system to be disassembled for transport and then re-assembled onsite at the mine site or field, the system including:
a compactable stand;
an imaging sensor for being supported by the stand; and
a transporter for transporting a geological sample, in the form of ore from the mine site or field, along a single axis to be sensed by the sensor, the transporter including a rail arrangement with a sole rail and a releasable carriage for moving along the sole rail.

Advantageously, the scanning system may be compact, and may be readily disassembled for transport and then re-assembled onsite in the field.

The stand may include retractable legs which can be retracted to compact the stand for transport. The legs may pivot and retract together. The stand may include a body extending up from the legs. The legs may be releasably fastened to the body and released to compact the stand for transport. The legs may include adjustable feet. The stand may include a rest upon which the transporter can rest. The stand may include another pair of legs.

The scanning system may further include a mount for mounting the sensor to the stand. The mount may include a cradle for cradling the sensor. The mount may be releasably fastened to the stand. The sensor may include a hyperspectral imaging sensor.

The transporter may further include a motor for driving the carriage along the rail arrangement. The carriage may include a platform. The transporter may include adjustable feet.

The scanning system may include a light for lighting the geological sample whilst being sensed by the sensor. The stand may include a mount for mounting the light to the stand.

The scanning system may be shipped in a container. The stand may be less than 1.5 metres high.

According to another aspect of the present invention, there is provided a method for setting up a geological sample scanning system, the method involving:
erecting a compactable stand;
mounting an imaging sensor to be supported by the stand; and
locating a transporter for transporting a geological sample along a single axis to be sensed by the sensor, the transporter including a rail arrangement with a sole rail and a releasable carriage for moving along the sole rail.

The step of erecting may involve expanding retracted legs. The step of erecting may involve attaching a body of the stand to the legs.

The step of mounting may involve mounting a sensor cradle to the stand. The step of mounting may involve mounting the sensor to the cradle.

The step of locating may involve locating a rail arrangement beneath the sensor. The step of locating may involve mounting a movable carriage for bearing a geological sample to the rail arrangement. The method may involve engaging the rail arrangement with the stand.

The method may further involve providing a light to light a geological sample transported by the transporter.

The method may involve adjusting feet of the stand and/or transporter. The method may involve transporting the scanning system, in disassembled form, in a shipping container.

Any of the features described herein can be combined in any combination with any one or more of the other features described herein within the scope of the invention.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows:

FIG. 1a is an upper perspective view of a geological sample scanning system in accordance with an embodiment of the present invention;

FIG. 1b is a plan view of the geological sample scanning system of FIG. 1a;

FIG. 1c is a side view of the geological sample scanning system of FIG. 1a; and

FIG. 1d is an end view of the geological sample scanning system of FIG. 1a.

DETAILED DESCRIPTION OF PREFERRED EMBODIMENTS

According to an embodiment of the present invention, there is provided a compact geological sample scanning system 100 for locating onsite in the mine site or field. The partially-assembled scanning system 100, without a hyper-spectral imaging sensor or scanner fitted, is shown in FIG. 1*a*.

FIG. 1*a* shows the assembled scanning system 100. The scanning system 100 includes a gantry stand 200. The elevated sensor (not shown) is supported by the upright stand 200. A mounting cradle 202 is provided for mounting the cradled sensor to the stand 200. The cradle 202 is releasably fastened to the top of the stand 200.

The scanning system 100 further includes a transporter 204 for linearly transporting or translating a geological sample whilst being sensed by the sensor above. Advantageously, the scanning system 100 is compact, and can be readily disassembled for transport and then re-assembled onsite in the field as described below.

The stand 200 includes four retractable legs 206 which can be retracted in pairs to compact the stand 200 for transport. Upon release of locking pins 208, each pair of slanted legs 206 can pivot relative to a Y-bracket 210 and be retracted compactly together.

The stand 200 also includes two straight bodies 212 extending up from the legs 206. The legs 206 are releasably fastened to the bodies 212 using fasteners 214, and can be released to further compact the stand 200 for transport.

The slanted legs 206 also include height-adjustable feet 216 to level the sensor on uneven ground. The stand 200 also includes a pair of rests 218, extending between the legs 206, upon which the transporter 204 can rest. The rests 218 can include guides or fasteners 220 for guiding or fastening the transporter 204.

The transporter 204 includes an elongate rail arrangement 222, and a platform carriage 224 for moving along the rail arrangement 222. The transporter 204 further includes a motor for controllably driving the carriage 224 along the rail arrangement 222. The geological sample rests on the carriage 224 as it passes under the sensor in the cradle 202 for downward scanning. Like the stand 200, the transporter 204 also includes height-adjustable feet 216 for stabilizing and levelling on uneven ground.

The scanning system 100 also includes a light for lighting the transported geological sample whilst being sensed by the sensor. The stand 200 includes a mount 226 for mounting the light to the stand 200.

FIGS. 1*b-d* show the compact dimensions of the scanning system 100. The erected stand 200 is less than 1500 mm high and 1000 mm wide. The transporter 204 is less than 2500 mm long. Comparable prior art systems are significantly bigger and non-modular. These known systems are built specifically to scan core samples and therefore do not have the same flexibility as the present system 100. The present system 100 is capable of packing down much smaller.

The disassembled scanning system 100 is shipped in an ISO shipping container to site. A method for setting up the geological sample scanning system 100 is now briefly described.

First, the stand 200 is erected. The retracted legs 206 are parted, and the vertical body 212 is attached to the expanded legs 206.

Next, the sensor is mounted to be supported atop the stand 200. The sensor cradle 202 is mounted to the stand 200. In turn, the sensor is mounted in the cradle 202 with its scanning beam facing downwards.

Next, the transporter 204 is located so that the transported geological sample is sensed by the sensor above. The rail arrangement 222 is placed beneath the sensor and engaged with the stand 200. The movable carriage 224 is mounted to the rail arrangement 222.

Next, a light is provided to light the geological sample transported by the transporter 204 to provide high scan quality.

Finally, the method involves height adjusting the feet 216 of the stand 200 and/or transporter 204.

The geological sample is loaded on the carriage 224 which moves beneath the elevated sensor whilst scanning.

Once testing is complete, the scanning system 100 may be readily disassembled, using the reverse steps, and transported in a shipping container once more.

A person skilled in the art will appreciate that many embodiments and variations can be made without departing from the ambit of the present invention.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims appropriately interpreted by those skilled in the art.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

The invention claimed is:

1. A geological sample scanning system to be disassembled for transport and then re-assembled onsite at a mine site or field, the system including:
   a compactable stand configured to support an imaging sensor, wherein the compactable stand includes a first pair of legs, the legs being pivotably coupled to each other using a fastening assembly; and
   a transporter coupled to the first pair of legs, the transporter being configured for transporting a geological sample, in the form of ore from the mine site or field, along a single axis to be sensed by the sensor, the transporter including a rail arrangement with a sole rail and a releasable carriage for moving along the sole rail, wherein, in response to release of the fastening assembly, the first pair of legs is configured to retract and pivot relative to the fastening assembly.

2. A geological sample scanning system as claimed in claim 1, wherein the compactable stand includes the fastening assembly, the fastening assembly includes a Y-bracket, a fastener and at least one locking pin pivotably coupling the Y-bracket to the first pair of legs such that the legs pivot about the Y-bracket together in response to release of the locking pin.

3. A geological sample scanning system as claimed in claim 2, further including a mount assembly configured to mount the imaging sensor, and a second pair of legs pivotably coupled to each other using a further fastening assembly, the second pair of legs being spaced apart from the first pair of legs by the mount assembly, wherein a first leg from the first pair of legs is configured to move together with a first leg from the second pair of legs, wherein a second leg from the first pair of legs is configured to move together with a second leg from the second pair of legs, and wherein the first legs move independently from the second legs.

4. A geological sample scanning system as claimed in claim 3, further including the imaging sensor supported by the stand, wherein the stand includes a body extending up from the legs, the body having a proximal end and a distal end, wherein the proximal end of the body is coupled to the mount assembly, wherein the distal end of the body is coupled to the Y-bracket using the fastener.

5. A geological sample scanning system as claimed in claim 4, wherein the fastener is configured to: releasably fasten legs to the body; and release the legs to thereby compact the stand for transport.

6. A geological sample scanning system as claimed in claim 1, wherein the legs include adjustable feet.

7. A geological sample scanning system as claimed in claim 3, wherein the stand includes a rest assembly upon which the transporter can rest, the rest assembly including a first rest and a second rest, wherein the first rest extends between and couples the first legs, wherein the second rest extends between and couples the second legs.

8. A geological sample scanning system as claimed in claim 3, wherein the first legs move together in response to release of the locking pin and independently from the second legs.

9. A geological sample scanning system as claimed in claim 8, wherein the mount assembly is releasably fastened to the stand.

10. A geological sample scanning system as claimed in claim 3, wherein the mount assembly includes a U-shaped cradle for cradling the sensor.

11. A geological sample scanning system as claimed in claim 3, further including a light for lighting the geological sample whilst being sensed by the sensor.

12. A geological sample scanning system as claimed in claim 11, wherein the mount assembly is configured for mounting the light to the stand.

13. A geological sample scanning system as claimed in claim 1, wherein the imaging sensor includes a hyperspectral imaging sensor.

14. A geological sample scanning system as claimed in claim 1, wherein the carriage is in the form of a flat tray.

15. A geological sample scanning system as claimed in claim 1, wherein the transporter includes height-adjustable feet.

16. A geological sample scanning system as claimed in claim 1, wherein the scanning system is configured to be shipped in a container and the stand is less than 1.5 metres high.

17. A method for setting up a geological sample scanning system, the method comprising:

erecting a compactable stand, the compactable stand including a first pair of legs, the legs being pivotably coupled to each other using a fastening assembly, wherein erecting the compactable stand comprises expanding the first pair of legs and pivoting the legs about the fastening assembly;

mounting an imaging sensor to be supported by the stand; and locating a transporter for transporting a geological sample along a single axis to be sensed by the sensor, the transporter including a rail arrangement with a sole rail and a releasable carriage for moving along the sole rail.

18. A method as claimed in claim 17, further comprising transporting the scanning system, in disassembled form, in a shipping container.

19. A method as claimed in claim 17, further comprising adjusting feet of the transporter.

20. A method as claimed in claim 17, further comprising lighting the geological sample transported by the transporter.

\* \* \* \* \*